United States Patent
Schiff et al.

(10) Patent No.: US 8,372,017 B2
(45) Date of Patent: Feb. 12, 2013

(54) MULTI-STRANDED TRACKABLE GUIDEWIRE

(75) Inventors: Jonathan David Schiff, Andover, MA (US); Samuel Joseph Akins, Tewksbury, MA (US)

(73) Assignee: General Electric Company, Schenectady, NY (US)

( * ) Notice: Subject to any disclaimer, the term of this patent is extended or adjusted under 35 U.S.C. 154(b) by 809 days.

(21) Appl. No.: 11/928,685

(22) Filed: Oct. 30, 2007

(65) Prior Publication Data

US 2009/0112128 A1    Apr. 30, 2009

(51) Int. Cl.
 *A61B 5/00* (2006.01)
(52) U.S. Cl. ............... 600/585; 264/103; 174/126.1
(58) Field of Classification Search ............ 600/585; 264/103; 174/126.1
 See application file for complete search history.

(56) References Cited

U.S. PATENT DOCUMENTS

| | | | |
|---|---|---|---|
| 4,857,675 A * | 8/1989 | Marancik et al. ............ 174/15.4 |
| 5,373,619 A * | 12/1994 | Fleischhacker et al. ......... 29/451 |
| 5,395,332 A | 3/1995 | Ressemann et al. |
| 5,497,784 A * | 3/1996 | Imran .......................... 600/585 |
| 5,569,196 A | 10/1996 | Muni et al. |
| 5,897,819 A | 4/1999 | Miyata et al. |
| 5,938,623 A | 8/1999 | Quiachon et al. |
| 6,461,370 B1 | 10/2002 | Gray et al. |
| 7,025,758 B2 | 4/2006 | Klint |
| 2002/0043118 A1 | 4/2002 | Claude |
| 2004/0116833 A1 * | 6/2004 | Kato et al. ..................... 600/585 |
| 2004/0243168 A1 * | 12/2004 | Ferrera et al. ................. 606/191 |
| 2006/0106443 A1 * | 5/2006 | Michael et al. .............. 607/122 |
| 2007/0055128 A1 | 3/2007 | Glossop |

OTHER PUBLICATIONS

"Act One—Asahi Cable Tube", retreived from the internet URL: ASAHI INTECC (http://www.asahi-intecc.com/medical_oem.product/cabletube.html), Jan. 2005.

* cited by examiner

*Primary Examiner* — Max Hindenburg
*Assistant Examiner* — Renee Danega
(74) *Attorney, Agent, or Firm* — Kenneth E. Horton; Kirton McConkie, PC

(57) ABSTRACT

A trackable guidewire is presented. The guidewire includes a plurality of wires arranged in a predetermined pattern to form a body of the guidewire, where the plurality of wires is configured to simultaneously provide electrical conductivity of signals and mechanical strength. A guidewire assembly is also presented, where the guidewire assembly includes a guidewire, where the guidewire includes a plurality of wires arranged in a predetermined pattern to form a body of the guidewire, and the plurality of wires is configured to simultaneously provide electrical conductivity of signals and mechanical strength, and one or more sensing devices, where the one or more sensing devices are operatively coupled to the guidewire. Methods of making the guidewire and the guidewire assembly are also contemplated in conjunction with the present technique.

21 Claims, 11 Drawing Sheets

MULTI-STRANDED TRACKABLE GUIDEWIRE

BACKGROUND

This disclosure relates generally to guidewires, and more particularly, to a system and method of integrating trackable elements into the guidewires for tracking the guidewires within vasculature of a patient.

A guidewire typically includes a flexible wire positioned in an organ, vessel, or duct of a patient for the purpose of directing passage of a larger device threaded over or along the length of the guidewire to a desired location in the vasculature of the patient. A wide variety of guidewires have been developed for various applications including medical applications, such as, but not limited to, coronary angioplasty. Also, endovascular interventions are rapidly advancing as a viable alternative for invasive vascular surgery. During these interventions, a guidewire is generally inserted into a region of a patient, such as the groin region, and the guidewire is then advanced to a desired location, typically under fluoroscopic guidance. Accurate positioning of the guidewire with respect to the vasculature is a prerequisite for a successful procedure. Furthermore, during neuro-interventions, positioning the guidewire accurately is difficult due to the complexity of the vasculature and narrowness of the blood vessels, thereby resulting in an increase of intervention time and exposure to radiation.

Recently, the guidewires have been known to include one or more tracking elements, such as but not limited to a sensing device, such as a microsensor. Surgical navigation systems may then be employed to track the location of the tip of the guidewire by tracking a location of the integrated microsensor, for example. A clinician may use the location information associated with the guidewire to efficiently navigate the guidewire to the desired location.

Numerous guidewires having integrated sensors have been developed. Unfortunately, incorporation of trackable sensors of high signal strength into devices of the sizes provided by typical guidewires having a diameter of less than 1 mm is an onerous task. Additionally, these trackable sensors may require a shielded type of electrical connection (e.g., coax or twisted pair) with the surgical navigation tracking system to reduce the introduction of noise into the electromagnetic signal. However, the introduction of the additional electrical connection disadvantageously results in the wires occupying precious real estate in the guidewire and hence reducing the real estate available for other connections. Furthermore, additional structural elements may be required to provide the desirable strength to the guidewire.

Moreover, one of the biggest challenges to the design of trackable guidewires is a method of attaching a trackable element to a distal end of the guidewire. The trackable element may include a microcoil, for example. One of the challenges with attaching the trackable element to the guidewire includes an electrical challenge. As will be appreciated, electrically, it may be desirable to have at least two electrically isolated conductors running from a start lead and a finish lead of the microcoil at the distal end of the guidewire, all the way down the length of the guidewire to a connection at a proximal end of the guidewire. These conductors may be used to energize a sensor coil, if it is a transmitter, or to pick up the induced signal if it is a receiver.

Also, a second challenge in attaching the trackable element to the distal tip of the guidewire may include a mechanical challenge. The leads running the length of the guidewire occupy precious real estate in the guidewire. As will be appreciated, there exist numerous applications for which it may be advantageous to maximize the amount of room available inside the guidewire. The room within the guidewire may be rendered hollow. Alternatively, a lumen may be created in the guidewire. Furthermore, it may be desirable to make the room within the guidewire available for other internal components of the guidewire, where the internal components may be configured to enhance steerability of the guidewire and/or to tailor flexibility of the guidewire. In addition, mechanically, it may also be desirable to imbue the guidewire with certain properties like flexibility, "pushability" (column strength) and torquability, which may vary according to the application for which the guidewire is being used.

It may therefore be desirable to develop a robust guidewire for systematically navigating the guidewire to the desired location. In particular, there is a need for a design of a guidewire that is configured to simultaneously provide electrical conductivity and mechanical strength to the guidewire. There also exists a need for efficiently coupling the trackable element to the guidewire with minimal impact on the performance of the guidewire during clinical applications.

BRIEF DESCRIPTION

In accordance with aspects of the present technique, a trackable guidewire is presented. The guidewire includes a plurality of wires arranged in a predetermined pattern to form a body of the guidewire, where the plurality of wires is configured to simultaneously provide electrical conductivity of signals and mechanical strength.

In accordance with further aspects of the present technique, a guidewire assembly is presented. The guidewire assembly includes a guidewire, where the guidewire comprises a plurality of wires arranged in a predetermined pattern to form a body of the guidewire, where the plurality of wires is configured to simultaneously provide electrical conductivity of signals and mechanical strength. Additionally, the guidewire assembly includes one or more sensing devices, where the one or more sensing devices are operatively coupled to the guidewire.

In accordance with another aspect of the present technique, a method of making a guidewire is presented. The method includes arranging a plurality of wires in a predetermined pattern to form a body of the guidewire, where the plurality of wires is configured to simultaneously provide electrical conductivity of signals and mechanical strength to the guidewire. In addition, the method includes disposing one or more electrical conductors in one or more wires in the plurality of wires. Furthermore, the method includes bonding the plurality of wires to form a cabled bundle of the wires.

In accordance with yet another aspect of the present technique, a method of making a guidewire assembly is presented. The method includes arranging a plurality of insulated wires in a predetermined pattern to form a body of the guidewire, where the plurality of wires is configured to simultaneously provide electrical conductivity of signals and mechanical strength to the guidewire. Furthermore, the method includes disposing one or more electrical conductors in one or more wires in the plurality of wires. In addition, the method includes bonding the plurality of wires to form a cabled bundle of the wires. Moreover, the method includes disposing one or more sensing devices at a predetermined location. The method also includes operationally coupling the one or more sensing devices to the wires in the guidewire.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As will be described in detail hereinafter, exemplary guidewires, exemplary guidewire assemblies having integrated sensors, and method for making the exemplary guidewires and the exemplary guidewire assemblies, where the guidewires may be configured to simultaneously allow substantially superior electrical and mechanical connection to a sensor assembly, are presented. Employing the methods and systems described hereinafter, the strands of wires in the guidewire may be employed as electronic circuit elements as well as mechanical structure elements.

Although, the exemplary embodiments illustrated hereinafter are described in the context of a medical imaging system, it will be appreciated that use of the guidewire in industrial applications are also contemplated in conjunction with the present technique.

Figure 1:
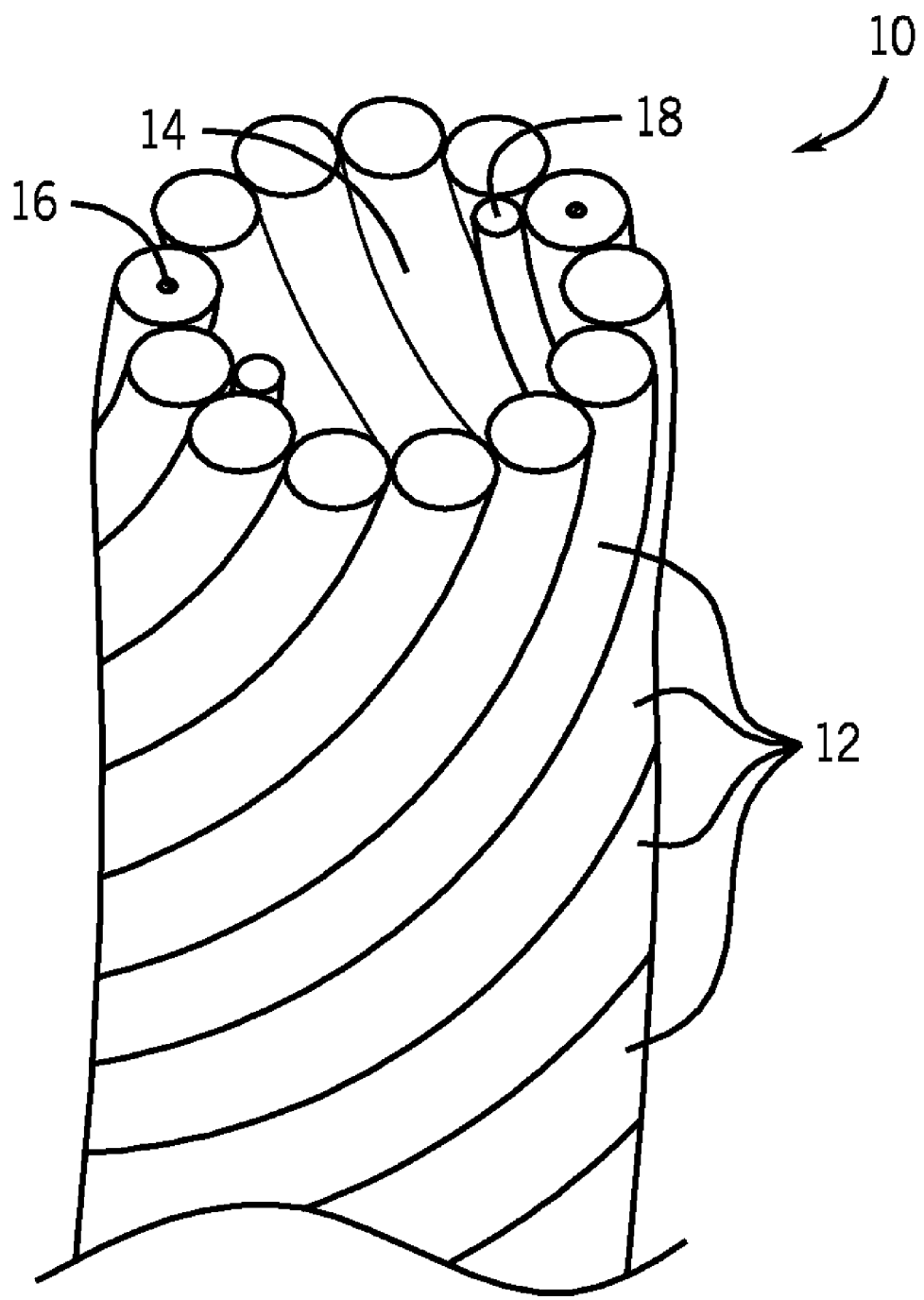
FIG. 1 is a diagrammatic illustration of an exemplary guidewire, in accordance with aspects of the present technique.

FIG. 1 depicts a diagrammatic illustration of an exemplary guidewire 10, in accordance with aspects of the present technique. As will be appreciated by one skilled in the art, the figures are for illustrative purposes and are not drawn to scale. The guidewire 10 may include a plurality of wires 12, where the plurality of wires 12 may be arranged in a predetermined pattern to form a body of the guidewire 10. More particularly, in accordance with aspects of the present technique, the plurality of wires 12 may be arranged in a closed shape to form the body of the guidewire 10. In a presently contemplated configuration, the closed shape may include a circular shape. However, as will be appreciated, the closed shape may also include other shapes, such as a triangular shape, a square shape, a rectangular shape, a pentagonal shape, a hexagonal shape, or an octagonal shape, to name a few. Furthermore, the plurality of wires 12 may be arranged around a solid core, in certain embodiments. Alternatively, in certain other embodiments, the plurality of wires 12 may be arranged around a hollow center. In the example illustrated in FIG. 1, the plurality of wires 12 is shown as being arranged such that the guidewire 10 has a lumen 14.

In accordance with aspects of the present technique, the plurality of wires 12 may include single strands of insulated wire, a coaxial wire, or both. In other words, each of the wires in the plurality of wires 12 may include a single strand of insulated wire or a coaxial wire. The wires 12 may be insulated with materials such as polyimide, Parylene, Teflon, or any other similar biocompatible materials such that the wires 12 are electrically isolated from one another and may carry separate electrical signals. The wires 12 may also include a hydrophilic coating to reduce friction during use. It may be noted that the wires 12 may have a diameter in a range from about 0.013 mm to about 0.5 mm. Also, the wires 12 may include wires made from the same material or from different material.

Additionally, in accordance with further aspects of the present technique, the wires 12 may be arranged such that the wires 12 run substantially parallel to one another for the length of the guidewire 10 in either a spiral coiled configuration or in a straight linear configuration. In the example illustrated in FIG. 1, the guidewire 10 is shown as including the wires 12 arranged in a spiral coiled configuration. By arranging the wires to be substantially parallel to one another, the mechanical strength of the guidewire may be enhanced. Additionally, in certain embodiment, a pitch of the wires 12 in the spiral coiled configuration may be decreased from a proximal end of the guidewire 10 to a distal end of the guidewire 10 to reduce distal stiffness and reduce trauma to blood vessels during use of the guidewire 10. It may be noted that this variable spiral pitch may be employed with or without a tapered core wire present.

In accordance with exemplary aspects of the present technique, the wires 12 may be configured to simultaneously provide electrical conductivity and mechanical strength to the guidewire 10. More particularly, the wires 12 may be configured to serve as electrical conductors for signals generated by a sensing device that may be operatively coupled to the guidewire 10. Accordingly, electrical conductors 16 may be disposed in one or more wires 12 in the guidewire 10. In the example illustrated in FIG. 1, the electrical conductors 16 are shown as being disposed within one or more wires 12. These electrical conductors 16 may be employed to facilitate electrical conductivity.

Moreover, in addition to facilitating electrical conductivity, the wires 12 may also be configured to simultaneously provide mechanical strength and structure to the guidewire 10. Other structural elements (not shown in FIG. 1) may also be interspersed in the wires 12, where these structural elements may be configured to provide additional mechanical properties to the guidewire 10. Furthermore, these structural elements may be selected based on desired mechanical properties of the guidewire 10. More particularly, a material and/or a shape of the structural elements may be selected based on the desired mechanical properties. For example, if it is desirable for the guidewire 10 to be mechanically stiff, then materials such as metal, glass, or hard plastic materials may be used as the structural elements. The metal structural elements may include steel or Nitinol structural elements, for example. Alternatively, if flexible and/or flimsy mechanical properties of the guidewire 10 are desired, then the structural elements may include soft plastic materials or soft metals. Furthermore, the structural elements may include strands, fibers, rods, spheres, or tubes, for example. Furthermore, these structural elements may be coupled to the insulated wires 12 via appropriate bonding methods, such as extrusion, heat bonding of wire insulation, or adhesive application.

Alternatively, the wires 12 themselves may be used as the structural elements. In the example illustrated in FIG. 1, the guidewire 10 is shown as including the plurality of wires 12, where only 2 wires are shown as including electrical conductors. As will be appreciated, a simple sensor, such as a sensor with two leads, calls for a minimum of 2 wires (insulated conductors) in the guidewire 10, accordingly entailing need for a minimum of 2 wires in the guidewire 10. In the present example of FIG. 1, only 2 wires include electrical conductors. In accordance with aspects of the present technique, the other wires without any electrical conductors may be configured to serve as structural elements, thereby enhancing the mechanical strength of the guidewire 10.

Furthermore, once the wires 12 are arranged in the predetermined pattern, the insulated wires 12 may be coupled to one another via use of bonding methods, for example. The bonding methods may include an extrusion or application of adhesion. In other words, the wires 12 may be bonded to form the body of the guidewire 10. These bonded wires may also be referred to as a cabled bundle of wires. Also, one or more optical fibers 18 may also be included in the guidewire 10, where the optical fibers 18 may be configured to facilitate sending and/or receiving light in the guidewire 10.

Figure 2:
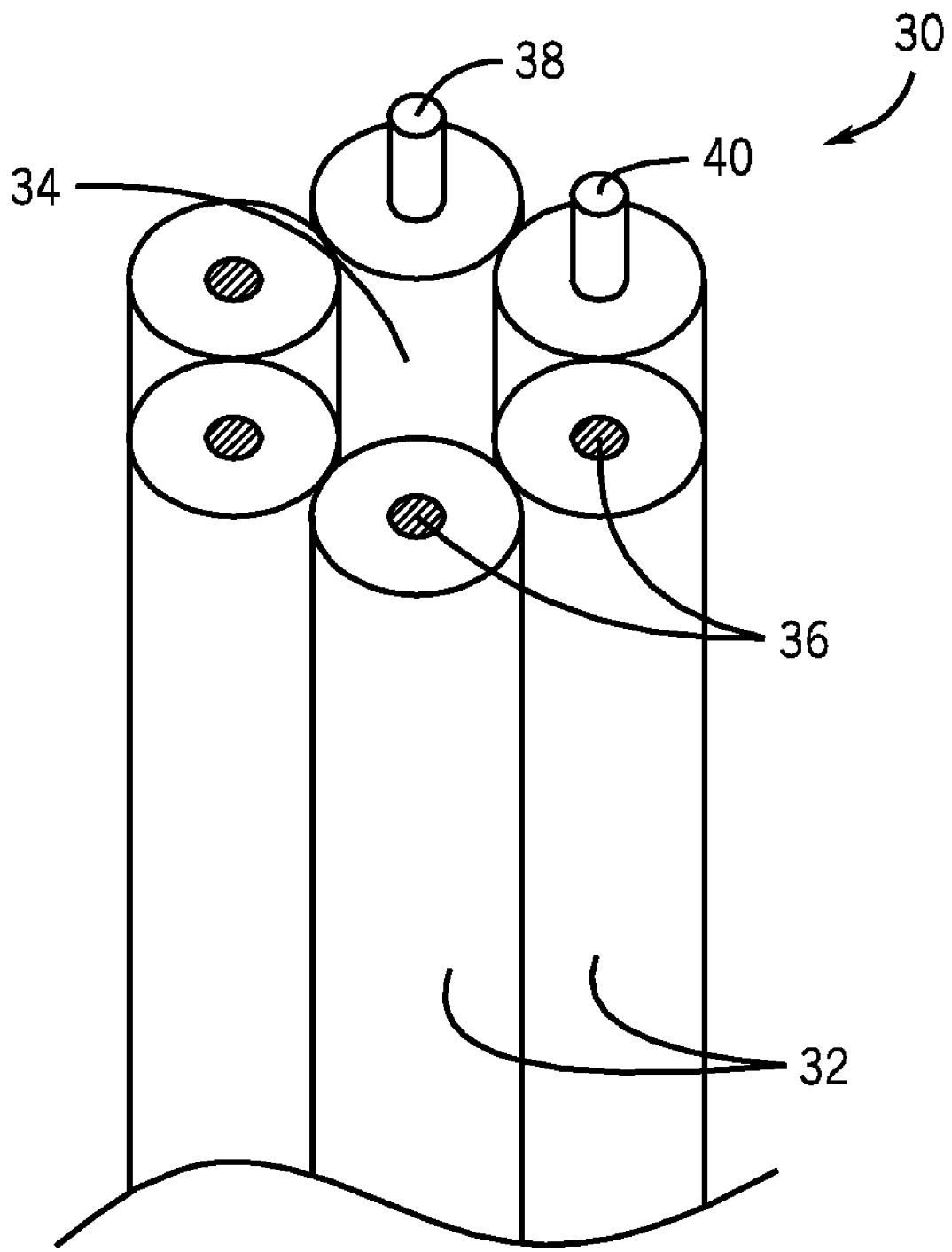
FIG. 2 is a diagrammatic illustration of another exemplary guidewire, in accordance with aspects of the present technique.

Turning now to FIG. 2, another embodiment of an exemplary guidewire 30 is illustrated. In the example illustrated in FIG. 2, the guidewire 30 is shown as having a plurality of wires 32 arranged in a predetermined pattern to form a body of the guidewire 30. Here again, the wires 32 may be arranged in a closed shape, such as a circular shape. Further, in the example illustrated in FIG. 2, the plurality of wires 32 is shown as being arranged such that the guidewire 30 has a lumen 34. Alternatively, the wires 32 may be arranged around a solid core that may or may not be tapered to reduce stiffness at a distal end of the guidewire 30. As previously noted, the wires 32 may include single strands of insulated wire, a coaxial wire, or both. The example of FIG. 2 shows the guidewire 30 as being formed by arranging a plurality of single strand wires 32.

As previously noted, in accordance with aspects of the present technique, the wires 32 may be arranged such that the wires 32 run parallel to one another for the length of the guidewire 30 in either a spiral coiled configuration or in a straight linear configuration. In the example illustrated in FIG. 2, the guidewire 30 is shown as including the wires 32 that are arranged in a straight linear configuration. Here again, the wires 32 may be insulated with materials such as polyimide, Parylene, Teflon, or any other similar biocompatible materials such that the wires 32 are electrically isolated from one another and may carry separate electrical signals. The wires 32 may also include a hydrophilic coating to reduce friction during use. It may be noted that the wires 32 may have a diameter in a range from about 0.013 mm to about 0.5 mm. Also, the wires 32 may include wires made from the same material or from different material. The insulated wires 32 may be coupled to one another via use of bonding methods, for example, to form the body of the guidewire 30. Also, these bonded wires 32 may generally be referred to as a cabled bundle of wires. Further, the bonding methods may include an extrusion or application of adhesion, as previously noted.

Here again, the wires 32 may be configured to simultaneously provide electrical conductivity and mechanical strength to the guidewire 30. More particularly, the wires 32 may be configured to serve as electrical conductors for signals generated by a sensing device that may be operatively coupled to the guidewire 30. Accordingly, as illustrated in the example of FIG. 2, electrical conductors 36 may be disposed within each of the wires 12, where the conductors may be employed to facilitate electrical conductivity. Although the example illustrated in FIG. 2 is shown as including an electrical conductor 36 within each wire 32, it may be appreciated that the electrical conductors 36 may also be disposed only within a subset of the wires 32. Also, as will be appreciated, at least one of the conductors 36 may be configured to provide a starting point to an electronic component (not shown in FIG. 2) that may be operatively coupled to the guidewire 30. Additionally, at least one other conductor 36 may be configured to provide an ending point to the electronic component that may be coupled to the guidewire 30. Accordingly, in one embodiment, a first wire 38 may be configured as the starting point for the electronic component, while a second wire 40 may be configured as the ending point for the electronic component. The first wire 38 may generally be referred to as a lead wire of the electronic component, while the second wire 40 may be representative of a return wire of the electronic component.

In addition to facilitating electrical conductivity, the wires 32 may also be configured to simultaneously provide mechanical strength and structure to the guidewire 30. Furthermore, additional structural elements (not shown in FIG. 2) may be interspersed in the wires 32 to provide additional mechanical strength, where the structural elements may include metal or plastic. Also, depending on an application of the guidewire 30, the guidewire 30 may be configured to be rigid or flexible. One or more optical fibers (not shown in FIG. 2) may also be included in the guidewire 30, where the optical fibers may be configured to facilitate sending and/or receiving light in the guidewire.

Figure 3:
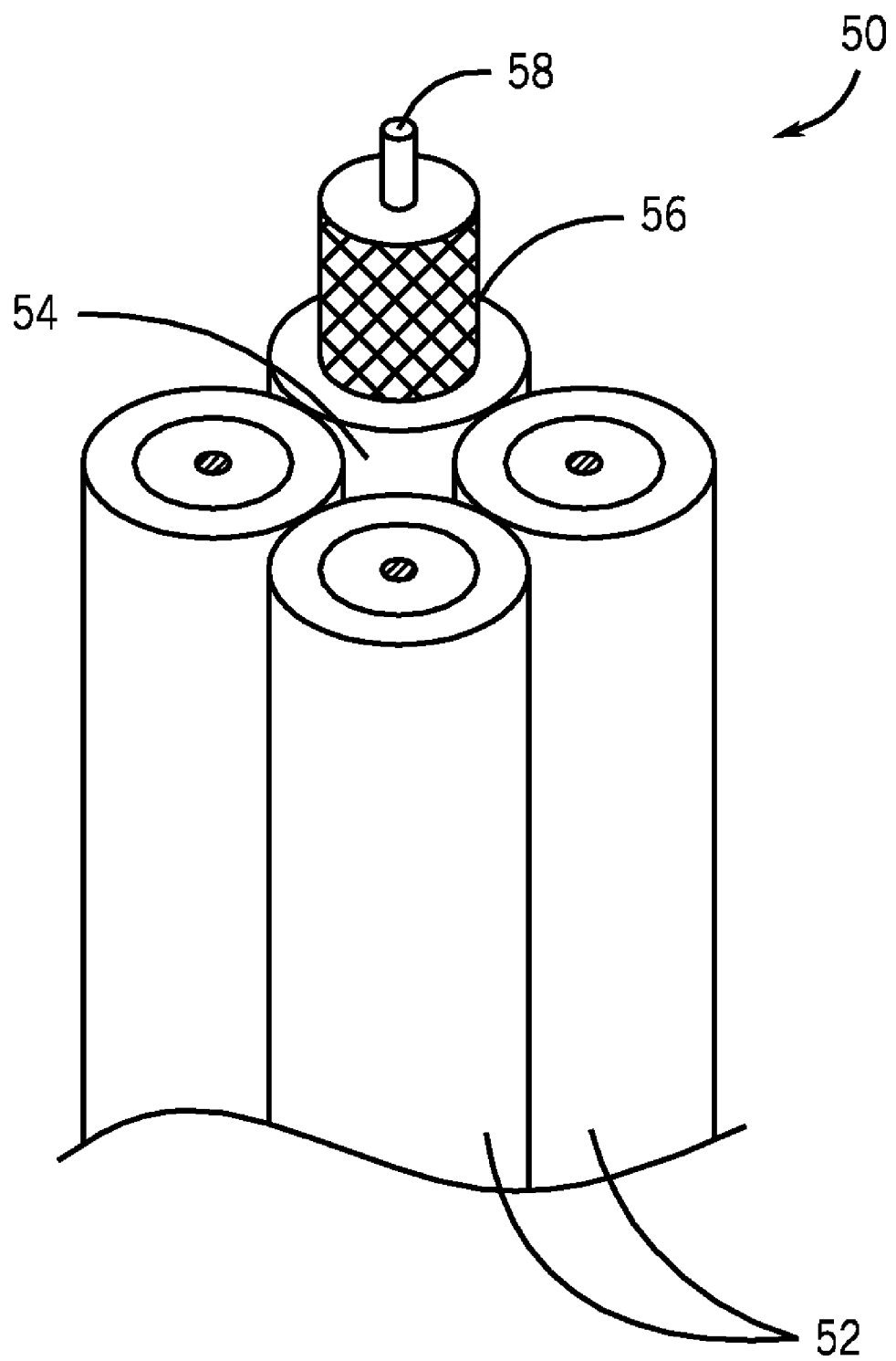
FIG. 3 is a diagrammatic illustration of yet another exemplary guidewire, in accordance with aspects of the present technique.

Referring now to FIG. 3, yet another embodiment of an exemplary guidewire 50 is illustrated. More particularly, FIG. 3 illustrates an alternate embodiment of the guidewire 30 of FIG. 2. In other words, the guidewire 50 may be formed by arranging a plurality of coaxial wires 52 in a predetermined pattern to form a body of the guidewire 50. Here again, the coaxial wires 52 may be arranged in a closed shape, such as a circular shape, as illustrated in FIG. 3. Additionally, a lumen in the guidewire 50 may generally be represented by reference numeral 54. Furthermore, in the example illustrated in FIG. 3, each of the wires 52 may include at least two conductors. In other words, each wire 52 may include a first conductor 56 and a second conductor 58. Although the embodiment illustrated in FIG. 3 shows the guidewire 50 as including a cabled bundle of coaxial wires 52, it may be noted that the guidewire 50 may also be formed by arranging a plurality of triaxial wires (not shown in FIG. 3) to form the body of the guidewire 50.

As previously noted, a guidewire is typically positioned in the vasculature of the patient to aid in navigating a catheter, for example, threaded over or along the length of the guidewire to a predetermined desired location. Furthermore, it may be desirable to track a current location of the guidewire to aid the clinician in directing/navigating the guidewire to the desired location. Systems, such as a surgical navigation system, may be employed to accurately track the current location of the guidewire. More particularly, the surgical navigation system may be configured to track the current location of the guidewire by tracking a current location of a trackable element, such as a sensing device, that may be operatively coupled to the guidewire. However, there exist electrical and mechanical challenges in efficiently attaching the trackable element to the guidewire.

Figure 4:
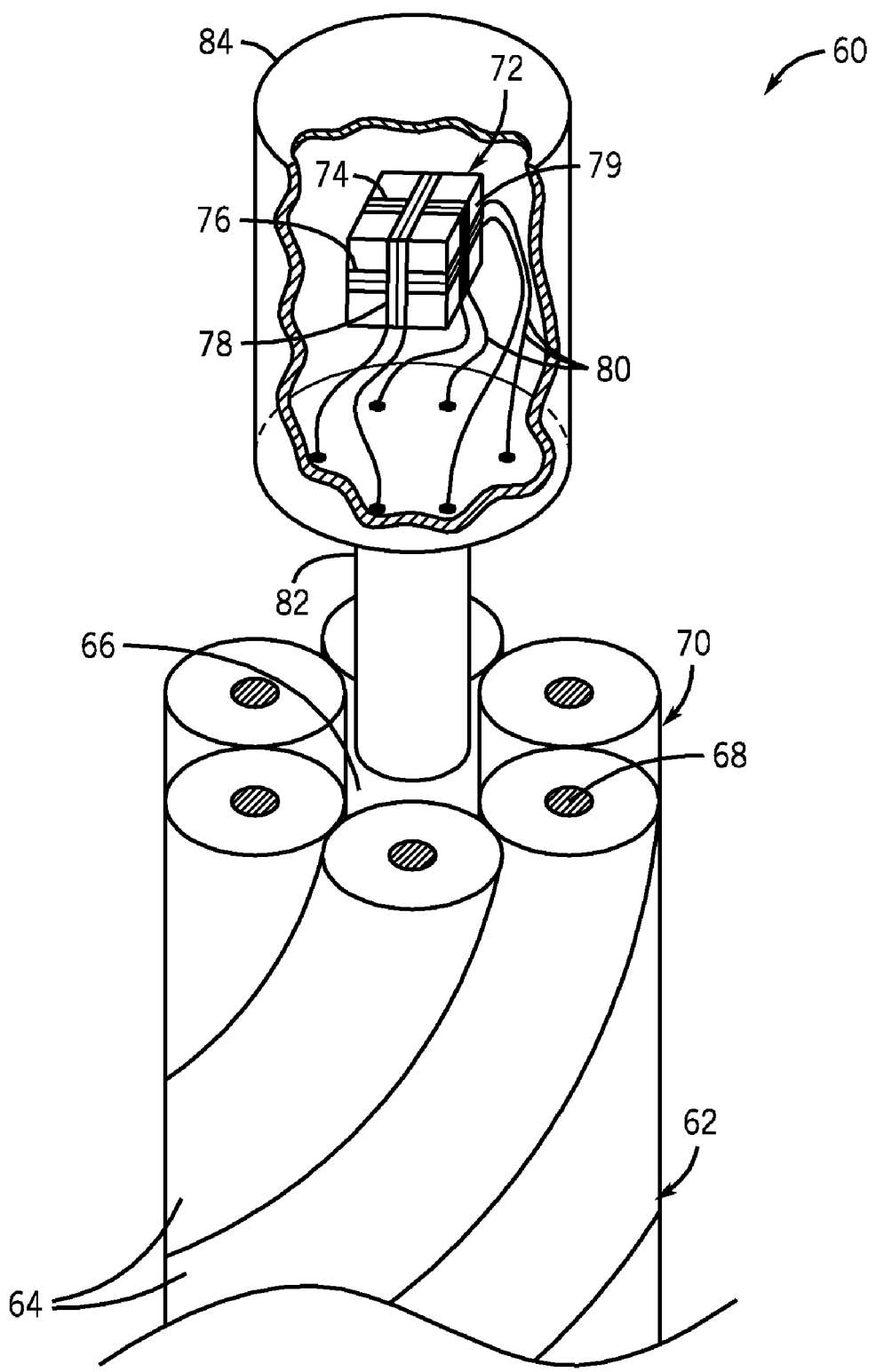
FIG. 4 is a diagrammatic illustration of an exemplary guidewire assembly with an integrated sensor, in accordance with aspects of the present technique.

In accordance with further aspects of the present technique, an exemplary guidewire assembly is presented, where the guidewire assembly may be configured to circumvent the shortcomings of the presently available guidewires. FIG. 4 depicts a diagrammatic illustration of an exemplary guidewire assembly 60. The term guidewire assembly may be used to refer to a device that includes the exemplary guidewire described hereinabove and at least one trackable element, such as a sensing device that is operationally coupled to the guidewire 62. In certain embodiments, the guidewire assembly 60 may include a guidewire having an integrated sensor assembly.

The guidewire assembly 60 may include a guidewire 62. In the example illustrated in FIG. 4, the guidewire 62 may include the guidewire 10 depicted in FIG. 1. In other words, the guidewire 62 may include a plurality of wires 64 arranged in a spiral coiled configuration to form a body of the guidewire 62. Reference numeral 66 may be representative of a lumen in the guidewire 62. Also, electrical conductors disposed within the wires 64 may generally be represented by reference numeral 68, where the electrical conductors 68 may be configured to facilitate conducting any electrical signals that may be generated by a sensing device that is operatively coupled to the guidewire 62. Further, the guidewire 62 may include a distal end 70 and a proximal end (not shown in FIG. 4).

Additionally, the guidewire assembly 60 may also include at least one trackable element. In certain embodiments, the at least one trackable element may include a sensing device. Also, the sensing device may include a sensor assembly 72, in one embodiment. In a presently contemplated configuration, the sensor assembly 72 may be disposed at the distal end 70 of the guidewire 62. Also, in accordance with aspects of the present technique, the sensor assembly 72 may include a trackable microcoil, an ultrasound transducer, a temperature sensor, a pressure sensor, a pH sensor, a sensing electrode, or other electrical components. Furthermore, in the example depicted in FIG. 4, the sensor assembly 72 is shown as including a microsensor. In certain embodiments, the microsensor may include three co-located sensor coils, as depicted in FIG. 4. In other words, the sensor assembly 72 may include a first sensor coil 74, a second sensor coil 76 and a third sensor coil 78.

Additionally, the sensor assembly 72 may be disposed within a protective outer casing 84, where the outer casing 84 may be configured to encapsulate the sensor assembly 72. This outer casing 84 may also include a molded tip. The outer casing 84 may be formed from a material, such as, but not limited to, biocompatible plastic such as urethane, polyethylene, acrylic, Teflon, or metals like stainless steel or Nitinol, for example.

Moreover, each of the sensor coils 74, 76, 78 may include a plurality of wire windings wound around a core 79. Additionally, each sensor coil 74, 76, 78 may also include a corresponding lead wire and a return wire extending from the corresponding plurality of wire windings. The lead wires and return wires corresponding to the three sensor coils 74, 76, 78 may generally be represented by reference numeral 80. These lead and return wires 80 may be brought out to exposed pads (not shown in FIG. 4) on an underside of the outer casing 84. In addition, these pads may be configured to make contact with exposed conductors, such as the conductors 68 in the cabled bundle of wires 64 of the guidewire 62. In certain embodiments the pads may be operatively coupled to the exposed conductors 68 in the guidewire 62 by soldering the pads to the exposed conductors 68. Alternatively, conductive epoxy may be used to operatively couple the pads to the exposed conductors 68. Furthermore, laser bonding and/or welding may also be used to operatively couple the pads to the exposed conductors 68.

In addition, the pads in the sensor assembly 72 may be aligned with the exposed conductors 68 in the guidewire 62 via use of an aligning mechanism 82. In other words, the sensor assembly 72 disposed within the outer casing 84 may be "keyed" with the guidewire 62 for substantially consistent orientation via use of the aligning mechanism 82.

In order to make the necessary electrical connections, at least two individual wires may be included in the cabled bundle of wires 64. Alternatively, a single coaxial wire may be included in the cabled bundle of wires 64 to provide the electrical connections. However, if more than one electronic component is disposed at the distal end 70 of the guidewire 62, and if it is desirable to electrically isolate circuitry associated with each component, then it may be desirable to include additional pairs of individual wires for each component. Alternatively, a single coaxial wire corresponding to each component may be included in the guidewire 62.

As will be appreciated, each microsensor typically requires a positive current lead and a return lead. However, multiple microsensors or sensor coils may be configured to share the same return lead. Accordingly, a common return for a plurality of return wires from the sensor coils 74, 76, 78 integrated within the guidewire 62 and a plurality of lead wires from the sensor coils 74, 76, 78 that extends through the guidewire 62 may be provided. Consequently, volume available in the guidewire 62 may be optimized by using a technique that minimizes the number of conductors needed to power individual microsensors 74, 76, 78. By reducing the number of leads for a given number of microsensors, the manufacturing process may be simplified. Additionally, the available volume in the guidewire 62 may be utilized for maximizing the number of microsensors that may be integrated into the guidewire 62.

In many applications, it may be desirable to make electrical connection with such a guidewire 62. More particularly, it may be desirable to make the electrical connection within the dimension of an outside diameter of the guidewire 62. In accordance with further aspects of the present technique, at the proximal end of a length of the cabled bundle of wires 64 in the guidewire 62, electrical connection may be made by exposing the conductors 68 at the proximal end of the guidewire 62, and providing a mating connector (not shown in FIG. 4) with a matching pattern of electrical contacts, one for each wire 64 in the guidewire 62. By implementing the guidewire 62 as described hereinabove, other devices, such as, but not limited to a catheter, for example, may be easily slid over the proximal end of the guidewire 62. Additionally, the mating connector may also be used to connect lead and return wires from the sensor assembly 72 to a surgical navigation system, for example.

By implementing the guidewire assembly 60 as described hereinabove, the electrical and mechanical requirements of the guidewire assembly 60 may be combined into one by using the same elements (wires 64) for conduction of electrical signals as are used for mechanical strength and structure. Each exemplary embodiment of guidewire 62 may be terminated at the proximal end using in-line connectors for connecting the lead and return wires 80 from the plurality of microsensors 74, 76, 78 integrated into the guidewire 62 to a surgical navigation system, for example.

Figure 5:
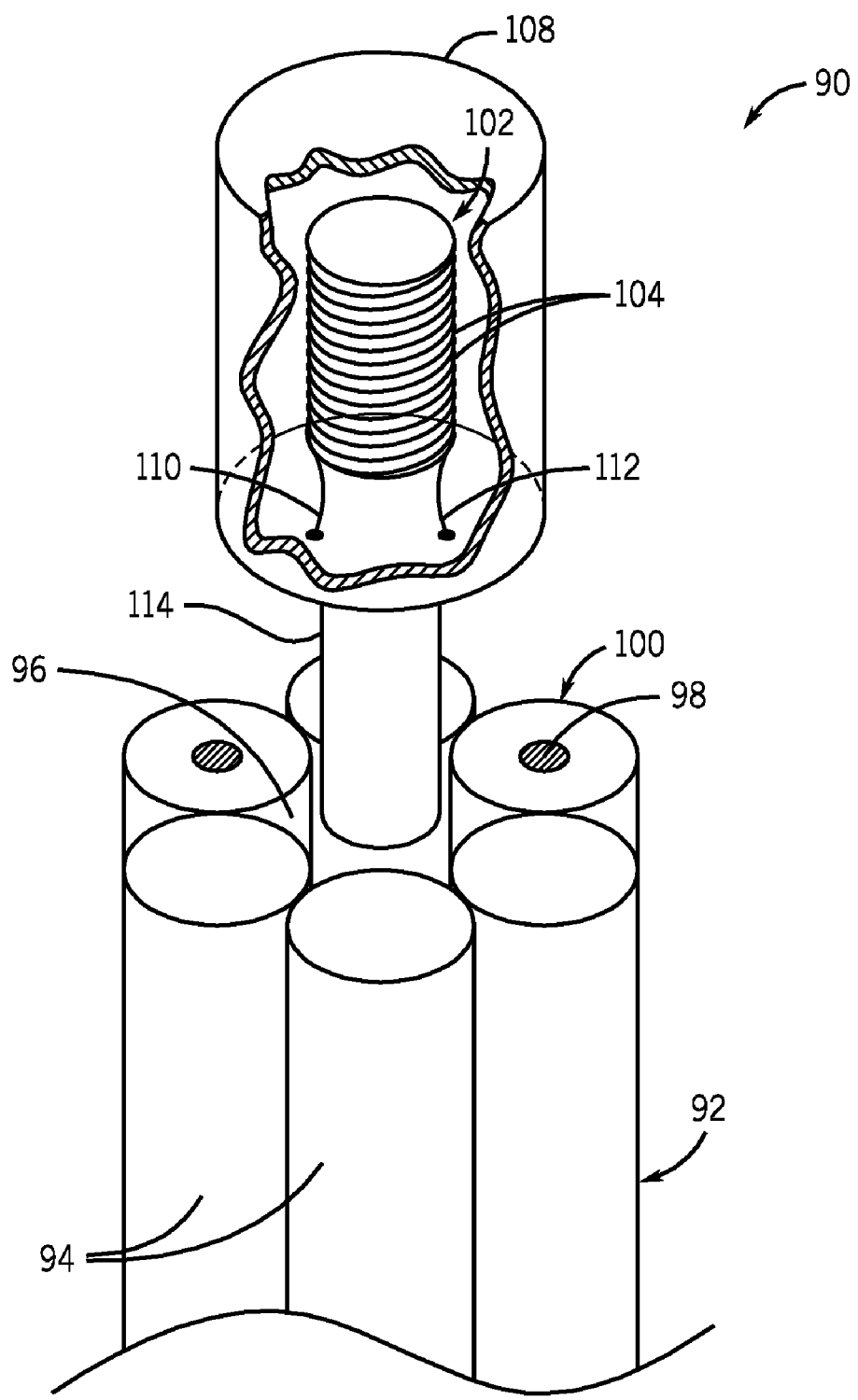
FIG. 5 is a diagrammatic illustration of another exemplary guidewire assembly with an integrated sensor, in accordance with aspects of the present technique.

Turning now to FIG. 5, in accordance with aspects of the present technique, another embodiment of an exemplary guidewire assembly 90 is illustrated. The guidewire assembly 90 may include a guidewire 92. Also, the guidewire 92 depicted in FIG. 5 may include a guidewire such as the guidewire 30 depicted in FIG. 2. More particularly, the guidewire 92 may include a plurality of wires 94 arranged in a straight linear configuration to form the body of the guidewire 92. Reference numeral 96 may be representative of a lumen in the guidewire 92. In addition, electrical conductors disposed within the wires 94 may generally be represented by reference numeral 98, where the electrical conductors 98 may be configured to facilitate conducting any electrical signals that may be generated by a sensing device that is operatively coupled to the guidewire 92. Further, the guidewire 92 may include a distal end 100 and a proximal end (not shown in FIG. 5).

As previously noted, the guidewire 92 may also include at least one trackable element, such as a sensing device 102, where the sensing device may include a sensor assembly, in certain embodiments. In a presently contemplated configuration, the sensor assembly 102 may be disposed at the distal end 100 of the guidewire 92. Also, in the present example illustrated in FIG. 5, the sensor assembly 102 may include a single microsensor 104.

Here again, the sensor assembly 102 may be disposed within a protective outer casing 108, where the outer casing 108 may be configured to encapsulate the sensor assembly 102. Also, the outer casing 108 may also include a molded tip. Further, the outer casing 108 may be formed from a material, such as, but not limited to, biocompatible plastic such as urethane, polyethylene, acrylic, Teflon, or metals such as stainless steel or Nitinol, for example.

Moreover, the single sensor coil 104 may include a plurality of wire windings wound around a core (not shown in FIG. 5). In addition, the sensor coil 104 may also include a corresponding lead wire 110 and a return wire 112 extending from the plurality of wire windings. These wires 110, 112 may be brought out to exposed pads (not shown in FIG. 5) on an underside of the outer casing 108. These pads may be configured to make contact with exposed conductors, such as the conductors 98 in the cabled bundle of wires 94 of the guidewire 92. In certain embodiments, the pads may be operatively coupled to the exposed conductors 98 in the guidewire 92 by soldering the pads to the exposed conductors 98. Alternatively, conductive epoxy may be used to operatively couple the pads and the exposed conductors 98.

Additionally, the pads in the sensor assembly 102 may be aligned with the exposed conductors 98 in the guidewire 92 via use of an aligning mechanism 114. In other words, the sensor assembly 102 disposed within the outer casing 108 may be "keyed" with the guidewire 92 for substantially consistent orientation via use of the aligning mechanism 114.

Here again, at the proximal end of a length of such a cabled bundle of wires 94 in the guidewire 92, electrical connection may be made by exposing the conductors 98 at the proximal end of the guidewire 92, and providing a mating connector (not shown in FIG. 5) with a matching pattern of electrical contacts, one for each wire 94 in the guidewire 92. By implementing the guidewire 92 as described hereinabove advantageously allows the guidewire 92 to make an electrical connection within the dimension of an outside diameter of the guidewire 92. Additionally, by implementing the guidewire 92 as described hereinabove, other devices, such as, but not limited to a catheter, for example, may be easily slid over the proximal end of the guidewire 92, as previously noted.

Figure 6:
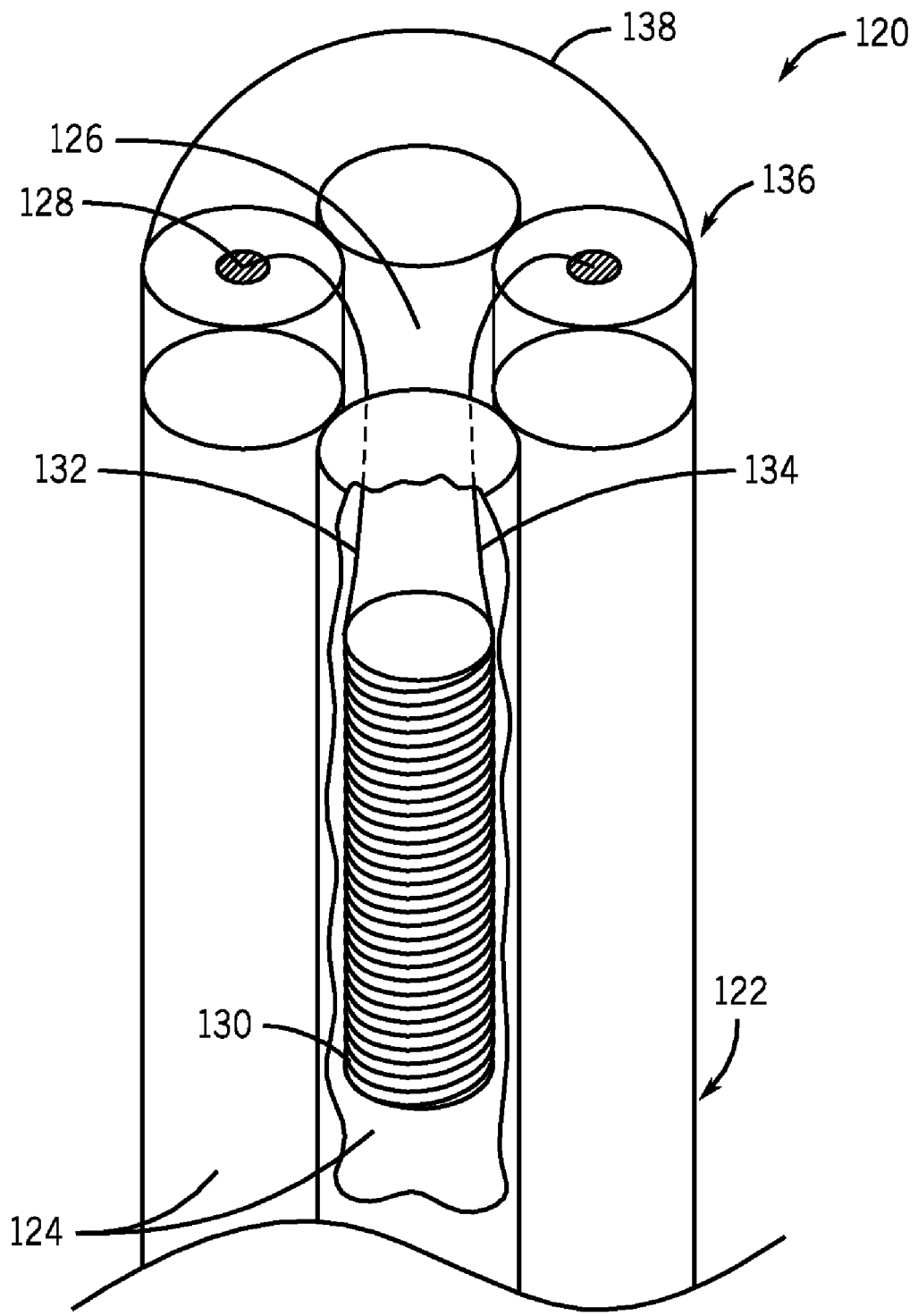
FIG. 6 is a diagrammatic illustration of yet another exemplary guidewire assembly with an integrated sensor, in accordance with aspects of the present technique.

FIG. 6 depicts a diagrammatic illustration of yet another embodiment of an exemplary guidewire assembly 120, in accordance with aspects of the present technique. The guidewire assembly 120 may include a guidewire 122, such as the guidewire 30 depicted in FIG. 2. Accordingly, the guidewire 122 may include a plurality of wires 124 arranged in a straight linear configuration to form the body of the guidewire 122. A lumen in the guidewire 122 may generally be represented by reference numeral 126. In addition, reference numeral 128 may be representative of electrical conductors disposed within the wires 124, where the electrical conductors 128 may be configured to facilitate conducting any electrical signals that may be generated by a trackable element, such as a sensing device that may be operatively coupled to the guidewire 122.

As previously noted, the guidewire 122 may also include at least one sensing device 130, where the sensing device 130 may include a sensor assembly, in certain embodiments. Also, in the present example illustrated in FIG. 6, the sensor assembly 130 may include a single microsensor. In a presently contemplated configuration, the single microsensor 130 may be disposed within the lumen 126 of the guidewire 122. In other words, the single microsensor 130 may be embedded along the length of the guidewire 122.

As will be appreciated, the single sensor coil 130 may include a plurality of wire windings wound around a core. In addition, the sensor coil 130 may also include a lead wire 132 and a return wire 134 extending from the plurality of wire windings of the sensor 130. These lead and return wires 132, 134 may be operatively coupled to the electrical conductors 128 disposed in the wires 124 of the guidewire 122. In certain embodiments, the lead and return wires 132, 134 may be operatively coupled to the exposed conductors 128 in the guidewire 122 by soldering the wires 132, 134 to the exposed conductors 128. Alternatively, conductive epoxy may be used to operatively couple the lead and return wires 132, 134 to the exposed conductors 128.

Furthermore, a distal tip of the guidewire 122 may be represented by reference numeral 136. In addition, a protective cover 138 may be disposed at the distal tip 136 of the guidewire 122. The protective cover 138 may include an electrical insulator in certain embodiments. Also, the protective cover 138 may be formed from a material, such as, but not limited to, biocompatible plastic such as urethane, polyethylene, acrylic, Teflon, or metals like stainless steel or Nitinol, for example.

As previously described with reference to FIGS. 4-5, at the proximal end of a length of such a cabled bundle of wires 124 in the guidewire 122, electrical connection may be made by exposing the conductors 128 at the proximal end of the guidewire 122, and providing a mating connector (not shown in FIG. 6) with a matching pattern of electrical contacts, one for each wire 124 in the guidewire 122. By implementing the guidewire 122 as described hereinabove advantageously allows the guidewire 122 to make an electrical connection within the dimension of an outside diameter of the guidewire 122. Additionally, by implementing the guidewire 122 as described hereinabove, other devices, such as, but not limited to a catheter, for example, may be easily slid over the proximal end of the guidewire 122. In addition, by implementing the guidewire 122 as described hereinabove, as the microsensor 130 is disposed within the lumen 126 of the guidewire 122 no additional mechanical support may be necessary, thereby advantageously saving precious real estate on the guidewire 122.

Figure 7:
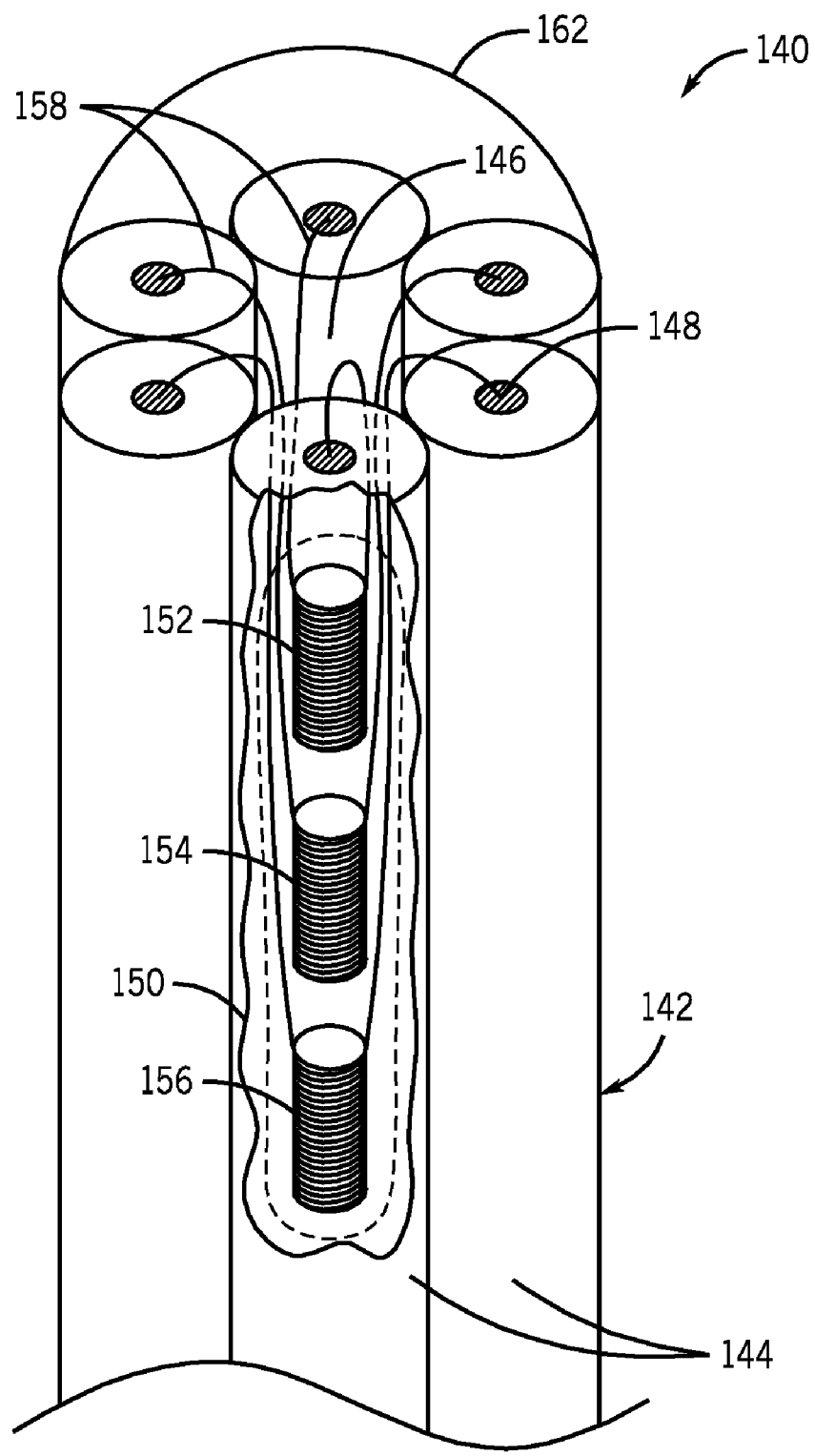
FIG. 7 is a diagrammatic illustration of another exemplary guidewire assembly with an integrated sensor, in accordance with aspects of the present technique.

Referring now to FIG. 7, a diagrammatic illustration of yet another embodiment of an exemplary guidewire assembly 140, in accordance with aspects of the present technique is illustrated. Here again, the guidewire assembly 140 may include a guidewire 142, such as the guidewire 30 depicted in FIG. 2. Hence, the guidewire 142 may include a plurality of wires 144 arranged in a straight linear configuration to form the body of the guidewire 142. Reference numeral 146 may generally be representative of a lumen in the guidewire 142. In addition, electrical conductors disposed within the wires 144 may generally be represented by reference numeral 148, where the electrical conductors 148 may be configured to facilitate conducting any electrical signals that may be generated by a sensing device that may be operatively coupled to the guidewire 142.

As previously noted, the guidewire 142 may also include at least one trackable element, such as a sensing device 150, where the sensing device 150 may include a sensor assembly, in certain embodiments. Moreover, in the present example illustrated in FIG. 7, the sensor assembly 150 may include three microsensors. More particularly, the sensor assembly 150 may include a first microsensor 152, a second microsensor 154 and a third microsensor 156. In a presently contemplated configuration, the three microsensors 152, 154, 156 in the sensor assembly 150 may be disposed within the lumen 146 of the guidewire 142. In other words, the microsensors 152, 154, 156 may be embedded along the length of the guidewire 142.

Furthermore, each of the three sensor coils 152, 154, 156 may include a respective plurality of wire windings wound around a corresponding core. In addition, the sensor coils 152, 154, 156 may also include corresponding lead wires and return wires extending from the corresponding plurality of wire windings. The lead and return wires corresponding to the sensor coils 152, 154, 156 may generally be represented by reference numeral 158. These lead and return wires 158 may be operatively coupled to the electrical conductors 148 disposed in the wires 144 of the guidewire 142. In certain embodiments, the lead and return wires 158 may be operatively coupled to the exposed conductors 148 in the guidewire 142 by soldering the lead and return wires 158 to the exposed conductors 148. Alternatively, conductive epoxy may be used to operatively couple the lead and return wires 158 to the exposed conductors 148.

In addition, a distal tip of the guidewire 142 may be represented by reference numeral 160. In addition, a protective cover 162 may be disposed at the distal tip 160 of the guidewire 142. The protective cover 162 may include an electrical insulator in certain embodiments. Also, the protective cover 162 may be formed from a material, such as, but not limited to, biocompatible plastic such as urethane, polyethylene, acrylic, Teflon, or metals like stainless steel or Nitinol, as previously noted.

Here again, as previously noted, each microsensor typically requires a positive current lead and a return lead. However, multiple microsensors or sensor coils may be configured to share the same return lead. Accordingly, a common return for a plurality of return wires from the sensor coils 152, 154, 156 integrated within the guidewire 142 and a plurality of lead wires from the sensor coils 152, 154, 156 that extends through the guidewire 142 may be provided. Consequently, volume available in the guidewire 142 may be optimized by using a technique that minimizes the number of conductors needed to power individual microsensors 152, 154, 156. By reducing the number of leads for a given number of microsensors, the manufacturing process may be simplified. Additionally, the available volume in the guidewire 142 may be utilized for maximizing the number of microsensors that may be integrated into the guidewire 142.

Furthermore, as previously described with reference to FIGS. 4-5, at a proximal end of a length of such a cabled bundle of wires 144 in the guidewire 142, electrical connection may be made by exposing the conductors 148 at the proximal end of the guidewire 142, and providing a mating connector (not shown in FIG. 7) with a matching pattern of electrical contacts, one for each wire 144 in the guidewire 142. By implementing the guidewire 142 as described hereinabove advantageously allows the guidewire 142 to make an electrical connection within the dimension of an outside diameter of the guidewire 142. Additionally, by implementing the guidewire 142 as described hereinabove, other devices, such as, but not limited to a catheter, for example, may be easily slid over the proximal end of the guidewire 142.

Moreover, by implementing the guidewire 142 as described hereinabove, as the microsensors 152, 154, 156 are disposed within the lumen 146 of the guidewire 142 no additional mechanical support may be necessary, thereby advantageously saving precious real estate in the guidewire 142. In addition, the mechanical performance of the guidewire 142 may be maintained by spacing a plurality of microsensors 152, 154, 156 along the length of the guidewire 142 and allowing additional flexibility between each microsensor 152, 154, 156 to compensate for the effective stiffness provided by each microsensor 152, 154, 156 and the corresponding wiring. The plurality of microsensors 152, 154, 156 efficiently occupy the volume available in the guidewire 142 to maximize the signal strength of each microsensor 152, 154, 156 without affecting the clinical and mechanical performance of the guidewire 142, especially with regards to pushability and steerability of the guidewire 142.

As previously noted, there exist mechanical and electrical challenges in attaching a trackable element to a guidewire. In accordance with aspects of the present technique, an exemplary method of making a guidewire that advantageously circumvents the electrical and mechanical challenges faced by the presently available guidewires is presented.

Figure 8A:
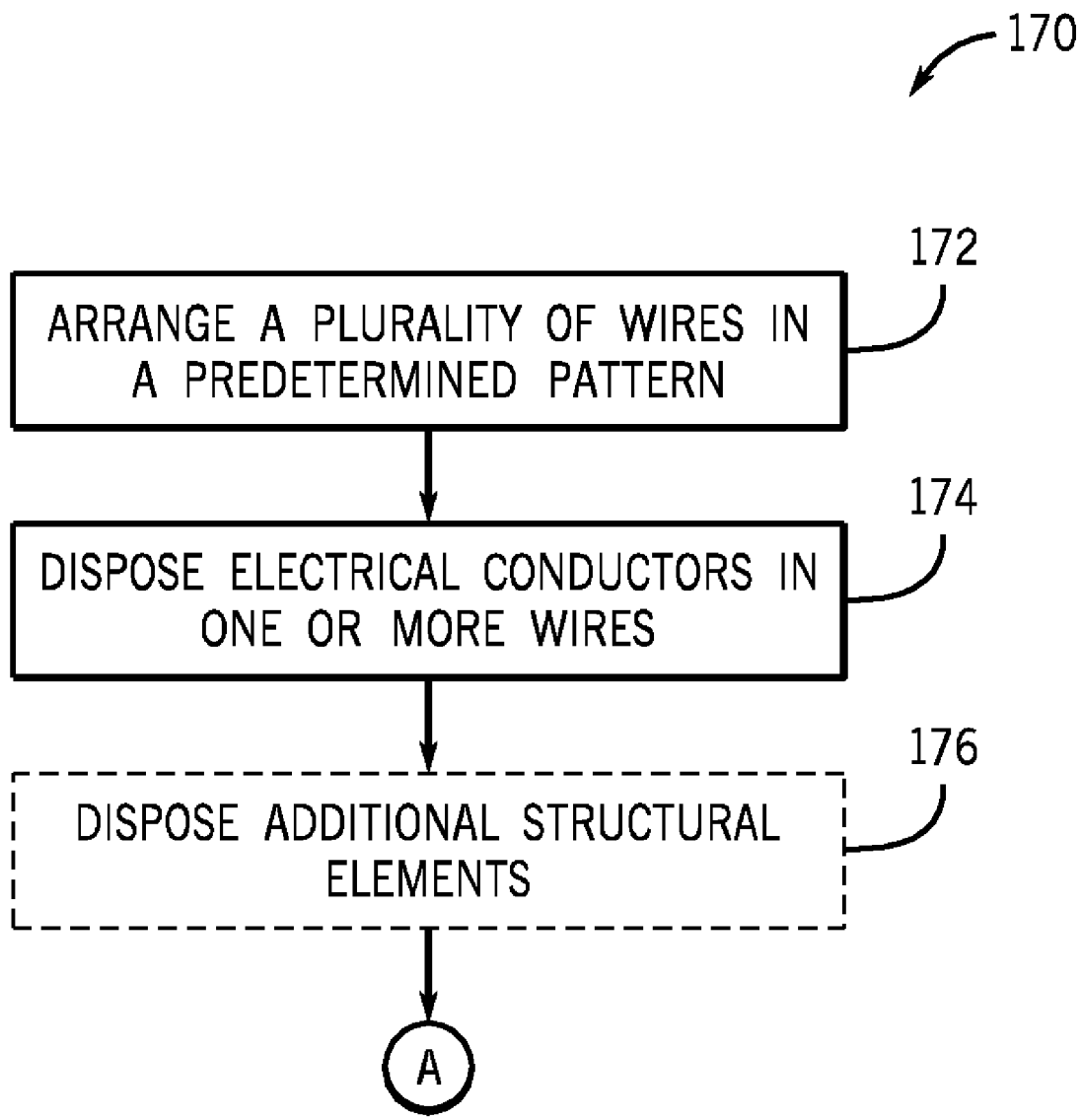
FIGS. 8A-8B are flow charts illustrating a process of making an exemplary guidewire, in accordance with aspects of the present technique.
Figure 8B:
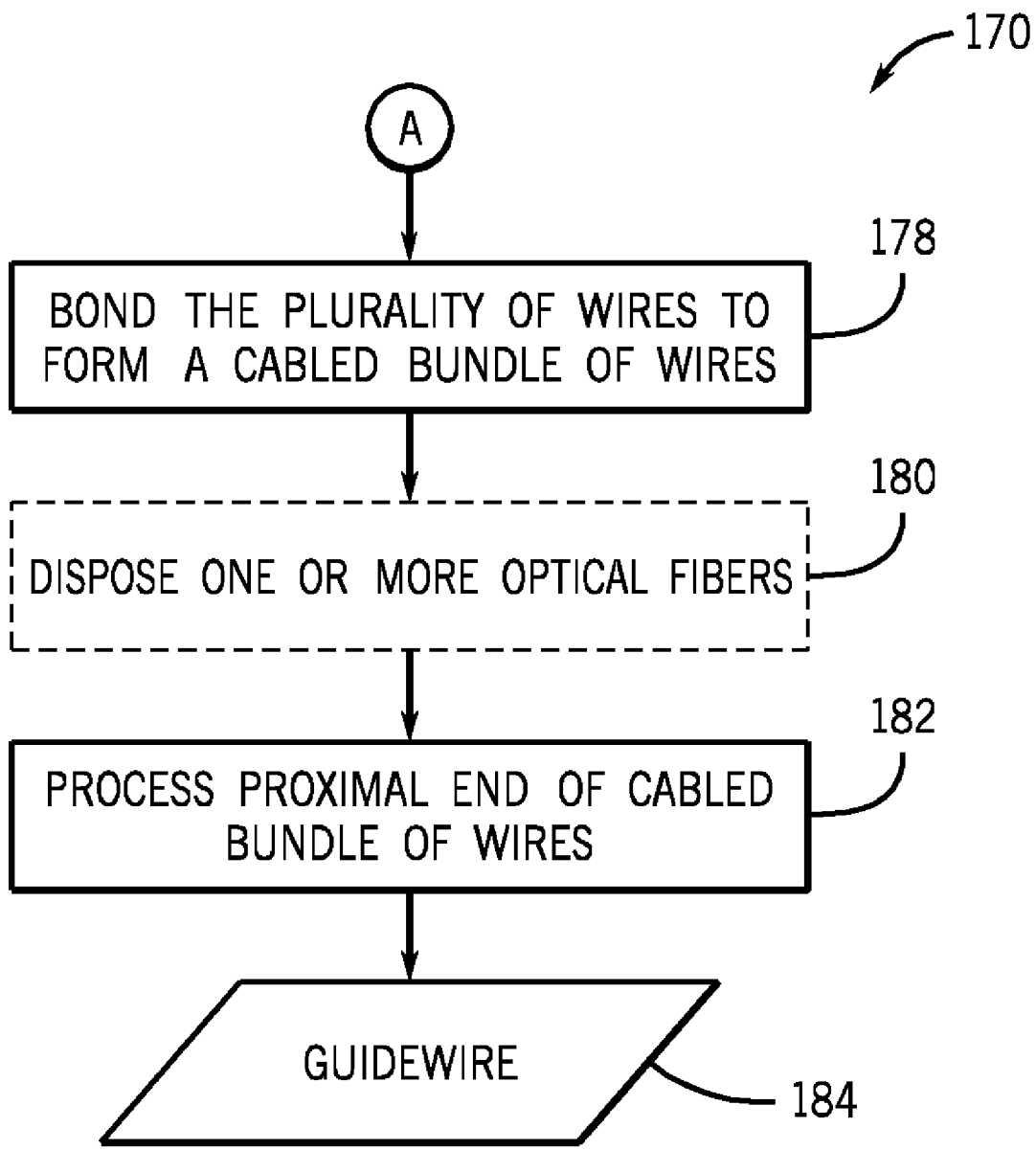

Turning now to FIGS. 8A-8B, a flow chart of exemplary logic 170 for making an exemplary guidewire, such as the guidewires 10 (see FIG. 1), 30 (see FIG. 2), 50 (see FIG. 3), is illustrated. The method starts at step 172 where a plurality of wires may be arranged in a predetermined pattern to form a body of the guidewire. It may be noted that in accordance with exemplary aspects of the present technique, the plurality of wires in the guidewire may be configured to simultaneously provide electrical conductivity of signals and mechanical strength.

The wires may include single strands of insulated wire or a coaxial wire. Also, the wires may be arranged around a solid core or a hollow center. Alternatively, the wires may be arranged such that a lumen is formed. Further, the wires may be arranged in the predetermined pattern, where the predetermined pattern may include a closed shape. In one embodiment, the wires may be arranged in a circular shape. Additionally, in accordance with further aspects of the present technique, the wires may be arranged such that the wires run substantially parallel to one another for the length of the guidewire in either a spiral coiled configuration (see FIG. 1) or in a straight linear configuration (see FIGS. 2-3). By arranging the wires to be substantially parallel to one another, the mechanical strength of the guidewire may be enhanced.

In accordance with exemplary aspects of the present technique, the wires may be configured to simultaneously provide electrical conductivity and mechanical strength to the guidewire. More particularly, the wires may be configured to serve as electrical conductors for signals generated by a sensing device that may be operatively coupled to the guidewire. These electrical conductors may be configured to facilitate providing electrical conductivity to signals that may be generated by one or more electronic components that may be operationally coupled to the guidewire. Accordingly, at step 174, electrical conductors may be disposed within one or more wires.

As previously noted, the wires in the guidewire may be configured to provide mechanical strength to the guidewire in addition to providing electrical conductivity. Accordingly, as depicted by optional step 176, one or more structural elements may be interspersed in the wires, where the structural elements may be configured to provide additional mechanical support/structural properties to the guidewire. The structural elements may include wires, strands, fibers, rods, or tubes, as previously noted. Also, the structural elements may include a metal or a plastic, for example. Furthermore, these structural elements may be coupled to the insulated wires via appropriate bonding methods, such as extrusion or adhesive application.

Once the wires are arranged in the predetermined pattern, the wires may be bonded to form a cabled bundle of wires, as indicated by step 178. In other words, the wires may be coupled to one another via use of bonding methods, for example. The bonding methods may include an extrusion or an application of adhesion. In other words, the wires may be bonded to form the body of the guidewire, where the guidewire includes a cabled bundle of wires. In addition, one or more optical fibers may also be included in the cabled bundle of wires, as depicted by optional step 180. These optical fibers may be configured to send and/or receive light through the guidewire.

Additionally, in many applications, it may be desirable to make electrical connection with a guidewire. More particularly, it may be desirable to make the electrical connection with a proximal end of the guidewire. Accordingly, at step 182, the proximal end of the cabled bundle of wires may be processed to facilitate this desirable connection. In other words, the electrical conductors in the wires may be exposed at the proximal end of the cabled bundle of wires. Further, a mating connector may be operationally coupled to the proximal end of the electrical conductors in the cabled bundle of wires, where the mating connector may be configured to have a matching pattern of electrical contacts. More particularly, the mating connector may be configured to include at least one electrical contact for each wire in the cabled bundle of wires. The mating connector may also be used to connect lead and return wires from a sensor and/or sensor assembly that may be operationally coupled to the guidewire to a surgical navigation system, for example. Consequent to processing by steps 172-182, an exemplary guidewire 184 may be formed, where the wires in the guidewire 184 may be configured to simultaneously provide electrical conductivity of signals and mechanical strength.

As previously noted, there exist mechanical and electrical challenges in attaching a trackable element to a guidewire. In accordance with aspects of the present technique, an exemplary method of making a guidewire assembly that advantageously circumvents the electrical and mechanical challenges faced by the presently available guidewire assemblies is presented. Here again, the term guidewire assembly may be used to refer to a device that includes the exemplary guidewire described hereinabove and at least one trackable element, such as a sensing device that may be in operative association with the guidewire.

Figure 9:
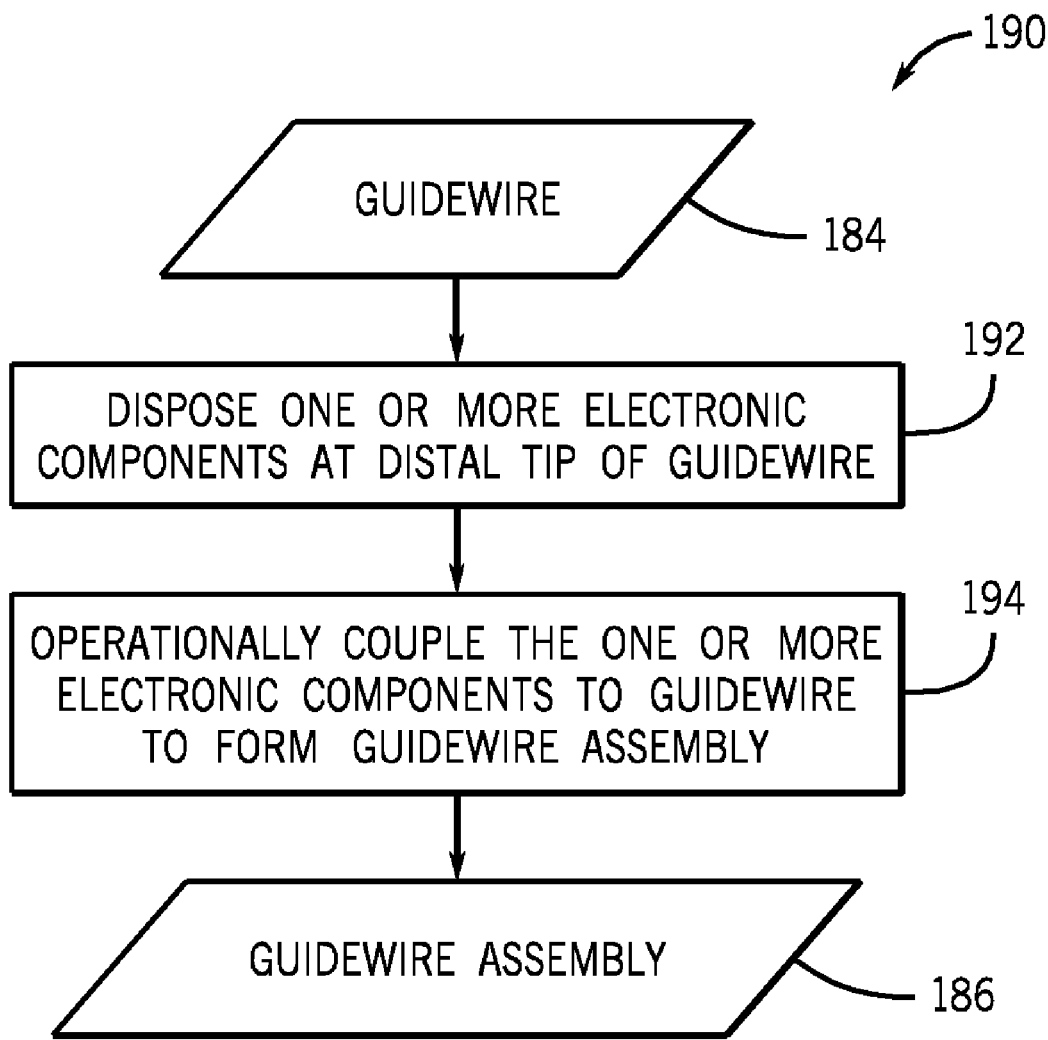
FIG. 9 is a flow chart illustrating a process of making an exemplary guidewire assembly, in accordance with aspects of the present technique.

In accordance with further aspects of the present technique, an exemplary method of making a guidewire assembly is presented. Referring now to FIG. 9, a flow chart of exemplary logic 190 for making an exemplary guidewire assembly, such as the guidewire assemblies 60 (see FIG. 4), 90 (see FIG. 5), is illustrated. More particularly, a method of forming a guidewire assembly by operationally coupling the guidewire to one or more sensing devices disposed at a distal tip of the guidewire is presented. The method starts at step 192 where one or more electronic components, such as sensing devices, may be disposed at a distal tip of the guidewire 184 (see FIG. 8).

As previously noted, the guidewire 184 may be formed by arranging a plurality of wires in a predetermined pattern, where the wires may be configured to simultaneously provide electrical conductivity of signals generated by a sensing device may be operationally coupled to the guidewire 184 and mechanical strength to the guidewire 184. More particularly, electrical conductors may be disposed in the wires to facilitate electrical conductivity.

Subsequently, at step 194, the one or more sensing devices may be operationally coupled to the electrical conductors in the wires of the guidewire. As previously noted, the sensing device may include a sensor assembly, where the sensor assembly may include one or more sensor coils, for example. Also, each sensor coil may include a respective plurality of windings wound around a corresponding core, for example. In addition, each sensor coil may include a corresponding lead wire and a return wire. It may be desirable to couple the lead and return wires of each sensor coil to the electrical conductors in the wires of the guidewire 184. Accordingly, the lead and return wires may be brought out to exposed pads. These pads may be configured to make contact with the exposed electrical conductors, such as the electrical conductors in the cabled bundle of wires of the guidewire 184. In certain embodiments, the pads may be operatively coupled to the exposed conductors in the guidewire by soldering the pads to the exposed conductors. Alternatively, conductive epoxy may be used to operatively couple the pads and the exposed conductors. Consequent to processing by steps 192-194, an exemplary guidewire assembly 196 may be formed, where the wires in the guidewire 184 may be configured to simultaneously provide electrical conductivity of signals and mechanical strength. The proximal end of this guidewire assembly 196 may then be coupled to a surgical navigation system, for example.

Figure 10:
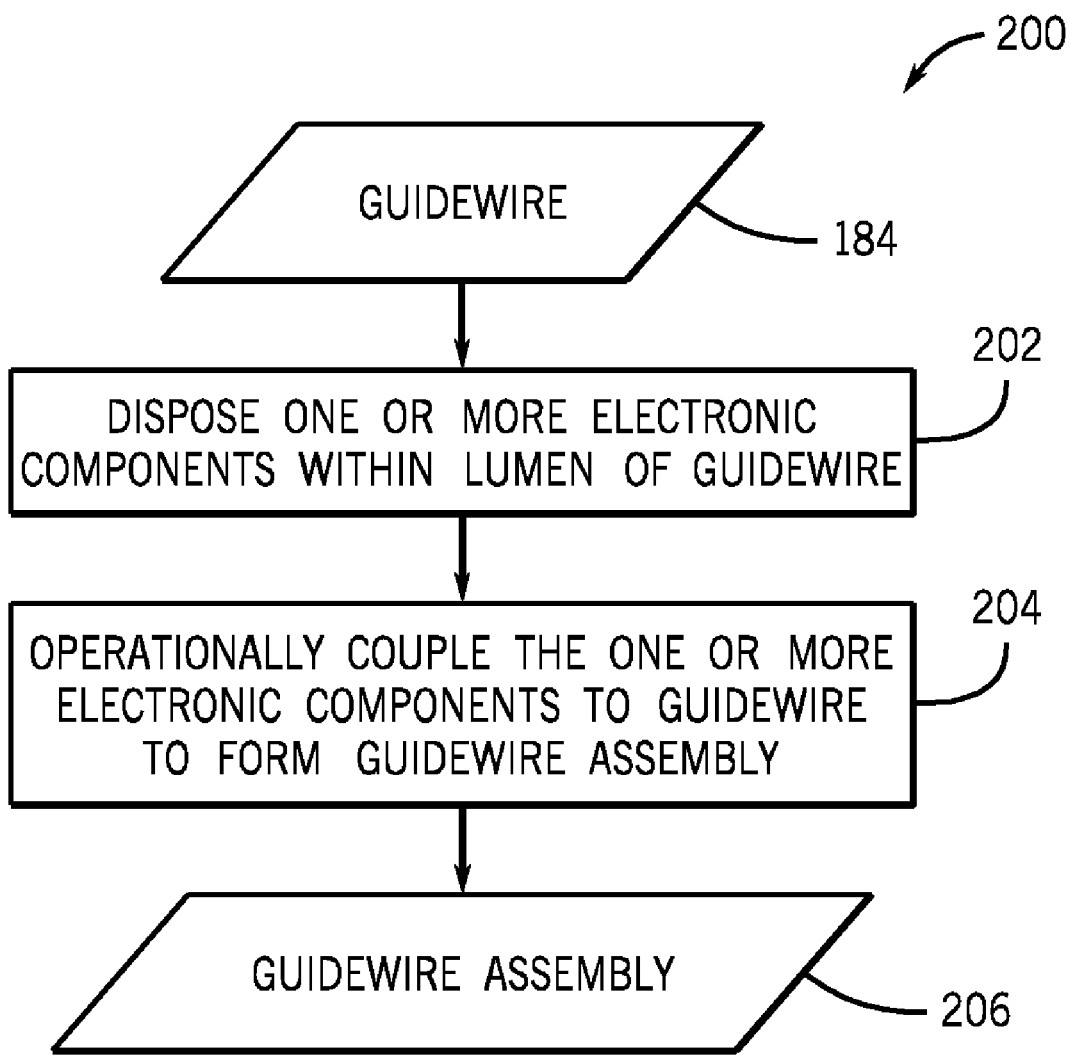
FIG. 10 is a flow chart illustrating a process of making another exemplary guidewire assembly, in accordance with aspects of the present technique.
Figure 7:
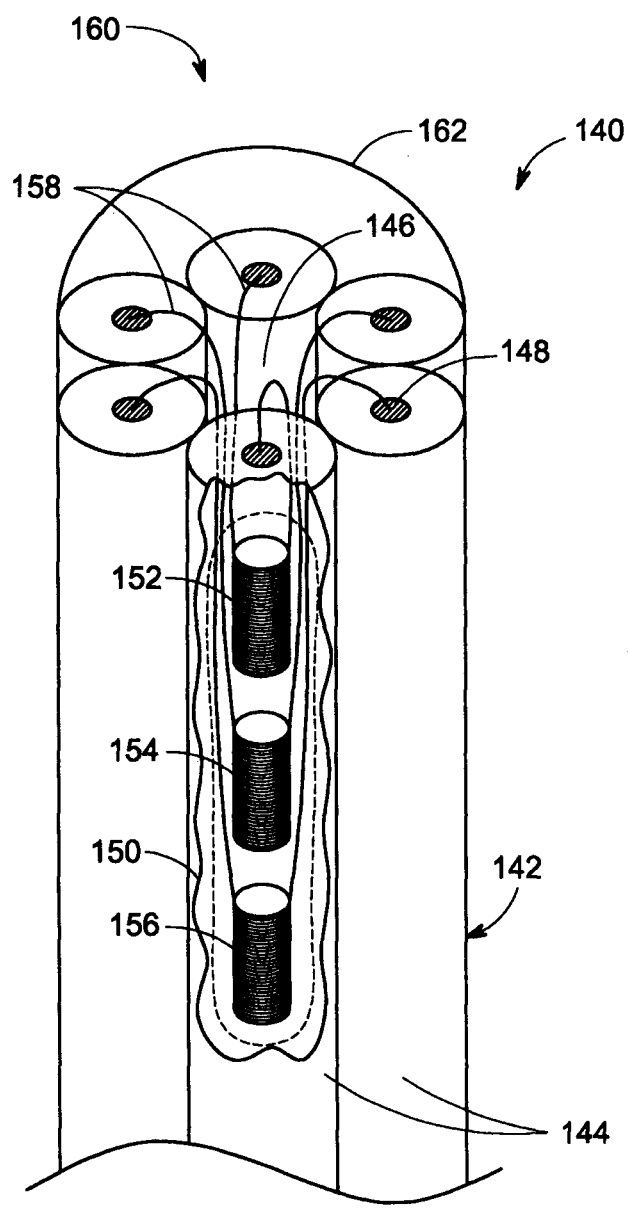

In accordance with further aspects of the present technique, another exemplary method of making a guidewire assembly is presented. Turning now to FIG. 10, a flow chart of exemplary logic 200 for making an exemplary guidewire assembly, such as the guidewire assemblies 120 (see FIG. 6), 140 (see FIG. 7), is illustrated. More particularly, a method of forming a guidewire assembly by operationally coupling the guidewire to one or more trackable elements, such as sensing devices disposed within a lumen of the guidewire is presented. The method starts at step 202 where one or more electronic components, such as sensing devices, may be disposed within a lumen of the guidewire 184 (see FIG. 8).

Here again, the guidewire 184 may be formed by arranging a plurality of wires in a predetermined pattern, where the wires may be configured to simultaneously provide electrical conductivity of signals generated by a sensing device and mechanical strength to the guidewire. Electrical conductors may be disposed in the wires to facilitate electrical conductivity.

Subsequently, at step 204, the one or more sensing devices disposed within the lumen of the guidewire may be operationally coupled to the electrical conductors disposed in the wires of the guidewire. As previously noted, the sensing device may include a sensor assembly, where the sensor assembly may include one or more sensor coils, for example. Also, each sensor coil may include a corresponding plurality of windings wound around a respective core, for instance. In addition, each sensor coil may include a corresponding lead wire and a return wire. It may be desirable to couple the lead and return wires of each sensor coil to the electrical conductors in the wires of the guidewire 184. Accordingly, the lead and return wires may be brought out to exposed pads. Also, these pads may be configured to make contact with exposed conductors, such as the conductors in the cabled bundle of wires of the guidewire 184. In certain embodiments, the pads may be operatively coupled to the exposed conductors in the guidewire by soldering the pads to the exposed conductors. Alternatively, conductive epoxy may be used to operatively couple the pads and the exposed conductors. Consequent to processing by steps 202-204, an exemplary guidewire assembly 206 may be formed, where the wires in the guidewire 184 may be configured to simultaneously provide electrical conductivity of signals and mechanical strength.

The exemplary guidewires, the guidewire assemblies, and the methods for making the guidewires and guidewire assemblies described hereinabove dramatically enhance electrical conductivity of the guidewires and the guidewire assemblies as well as the mechanical strength of the guidewires and the guidewire assemblies as the strands of wire may be used both as mechanical structure elements and electronic circuit elements. Further, by bonding the wires together and forming a (hollow) tubular bundle, desired mechanical properties of pushability and torquability of the guidewire may be realized. In addition, by electrically insulating each of the wires in the cabled bundle of wires, the guidewire may be employed as an electronic circuit that presents novel connection possibilities for sensors attached to the distal tip and/or embedded along the length of the guidewire.

Furthermore, by integrating the sensing devices into the guidewires in a robust and clinically effective way, minimally invasive surgical techniques and interventional procedures may utilize electromagnetic tracking technology to provide more efficient treatments, less radiation dose, and faster procedures. Also, the exemplary embodiments of guidewires described herein may be used as part of a surgical navigation system employing electromagnetic tracking technology that may be used in an interventional suite. The surgical navigation system may be integrated into a fixed C-arm system, a portable C-arm system, or a stand-alone tracking system.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of making a guidewire, the method comprising:
  arranging a plurality of wires in a predetermined pattern having a closed shape with the wires contacting each other, forming an interior lumen, and forming a body of the guidewire, wherein the plurality of wires is configured to simultaneously provide electrical conductivity of signals and mechanical strength to the guidewire;
  disposing one or more electrical conductors in one or more wires in the plurality of wires; and
  bonding the plurality of wires to form a cabled bundle of wires.

2. The method of claim 1, wherein wires in the cabled bundle of wires comprise single strands of insulated wire, a coaxial wire, or a combination thereof.

3. The method of claim 1, wherein arranging the plurality of wires in the cabled bundle of wires comprises disposing the plurality of wires in a substantially parallel arrangement for a length of the guidewire.

4. The method of claim 1, further comprising dispersing structural elements in the cabled bundle of wires, wherein the structural elements are configured to provide mechanical properties to the guidewire.

5. The method of claim 1, further comprising disposing optical fibers in the cabled bundle of wires.

6. The method of claim 1, further comprising disposing aligning means within the guidewire, wherein the aligning means are configured to orient the one or more sensing devices within the guidewire.

7. A method of making a guidewire assembly, the method comprising:
  arranging a plurality of insulated wires in a predetermined pattern having a closed shape with the wires contacting each other, forming an interior lumen, and forming a body of the guidewire, wherein the plurality of wires is configured to simultaneously provide electrical conductivity of signals and mechanical strength to the guidewire;
  disposing one or more electrical conductors in one or more wires in the plurality of wires;
  bonding the plurality of wires to form a cabled bundle of wires;
  disposing one or more sensing devices at a predetermined location; and
  operatively coupling the one or more sensing devices to the electrical conductors in the wires of the guidewire.

8. The method of claim 7, wherein the predetermined location comprises a distal tip of the guidewire, a lumen in the guidewire, or both.

9. The method of claim 1, further comprising disposing one or more sensing in the guidewire.

10. The method of claim 9, wherein the one or more sensing devices are disposed at a distal end of the guidewire.

11. The method of claim 9, wherein the one or more sensing devices are disposed within the lumen of the guidewire.

12. The method of claim 7, further comprising dispersing structural elements in the cabled bundle of wires, wherein the structural elements are configured to provide mechanical properties to the guidewire.

13. The method of claim 7, further comprising disposing optical fibers in the cabled bundle of wires.

14. The method of claim 8, wherein the one or more sensing devices are disposed at a distal end of the guidewire.

15. The method of claim 8, wherein the one or more sensing devices are disposed within the lumen of the guidewire.

16. The method of claim 7, further comprising disposing aligning means within the guidewire, wherein the aligning means are configured to orient the one or more sensing devices within the guidewire.

17. A method of making a guidewire, comprising:
  arranging a plurality of wires in a predetermined pattern having a closed shape with the wires contacting each other, forming an interior lumen, and forming a body of the guidewire, wherein the plurality of wires is configured to simultaneously provide electrical conductivity of signals and mechanical strength to the guidewire;
  disposing one or more electrical conductors in one or more wires in the plurality of wires;
  bonding the plurality of wires to form a cabled bundle of wires; and
  disposing one or more sensing devices in the guidewire.

18. The method of claim 17, further comprising coupling the one or more sensing devices to the one or more electrical conductors.

19. The method of claim 17, wherein the one or more sensing devices are disposed at a distal end of the guidewire.

20. The method of claim 17, wherein the one or more sensing devices are disposed within a lumen of the guidewire.

21. The method of claim 17, further comprising disposing aligning means within the guidewire, wherein the aligning means are configured to orient the one or more sensing devices within the guidewire.

* * * * *

UNITED STATES PATENT AND TRADEMARK OFFICE
CERTIFICATE OF CORRECTION

PATENT NO.       : 8,372,017 B2                                   Page 1 of 2
APPLICATION NO.  : 11/928685
DATED            : February 12, 2013
INVENTOR(S)      : Schiff et al.

It is certified that error appears in the above-identified patent and that said Letters Patent is hereby corrected as shown below:

In the Drawings

Fig. 7 should be replaced with the corrected Fig. 7, as shown as on the attached page.

In the Specification

In Column 6, line 3, please delete "12" and replace with --32--.
In Column 14, line 35 and 39, please delete "196" and replace with --186--.

Signed and Sealed this
Eleventh Day of February, 2014

Michelle K. Lee
*Deputy Director of the United States Patent and Trademark Office*